(12) United States Patent
Hastings et al.

(10) Patent No.: US 8,122,594 B2
(45) Date of Patent: Feb. 28, 2012

(54) METHOD OF MANUFACTURING A DEFLECTABLE ELECTROPHYSIOLOGICAL CATHETER

(75) Inventors: John M. Hastings, Minneapolis, MN (US); Gary B. LaTraille, Maple Grove, MN (US); Elizabeth Younger, Columbia Heights, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1087 days.

(21) Appl. No.: 11/967,390

(22) Filed: Dec. 31, 2007

(65) Prior Publication Data

US 2009/0171273 A1 Jul. 2, 2009

(51) Int. Cl.
*H05K 3/30* (2006.01)
*A61M 31/00* (2006.01)
(52) U.S. Cl. ........... 29/832; 29/854; 29/857; 29/863; 29/868; 604/95.04
(58) Field of Classification Search .......... 29/832, 29/746, 747, 748, 854, 857, 863, 868; 607/95.04, 607/105, 113, 122; 600/439, 374, 381, 27; 606/41, 62; 604/95.04
See application file for complete search history.

(56) References Cited

U.S. PATENT DOCUMENTS

| | | | |
|---|---|---|---|
| 5,395,328 A * | 3/1995 | Ockuly et al. | 604/528 |
| 5,938,694 A * | 8/1999 | Jaraczewski et al. | 607/122 |
| 7,218,958 B2 | 5/2007 | Rashidi | |
| 7,245,955 B2 | 7/2007 | Rashidi | |
| 2003/0014008 A1 * | 1/2003 | Jacques | 604/96.01 |
| 2006/0149336 A1 | 7/2006 | Meadows | |
| 2006/0184108 A1 | 8/2006 | Honebrink | |
| 2007/0156133 A1 | 7/2007 | McDaniel et al. | |

FOREIGN PATENT DOCUMENTS

EP 0 565 996 A1 10/1993

OTHER PUBLICATIONS

International Search Report and Written Opinion for PCT/US2008/086561 Mailed Feb. 23, 2009.

* cited by examiner

*Primary Examiner* — Derris Banks
*Assistant Examiner* — Tai Nguyen
(74) *Attorney, Agent, or Firm* — Dykema Gossett PLLC

(57) ABSTRACT

A method of manufacturing a deflectable electrophysiological catheter includes constructing a shaft having a distal end and at least one lumen. The method further includes inserting a component into the lumen, and processing at least a portion of the distal end to reduce the cross-sectional profile of the lumen to capture/confine the component. A catheter manufactured using this method includes a shaft having at least one lumen. The lumen comprises a longitudinally-extending trough defined by a longitudinally-extending recess, within which a component is disposed, and a longitudinally extending open edge. The lumen further comprises a longitudinally-extending channel defined by a longitudinally-extending cavity and by the open edge of the trough. A planarity wire is disposed within the cavity and is configured to close the open edge of the trough to within a pre-defined tolerance that is less than the size of the component to retain the component in the recess.

16 Claims, 5 Drawing Sheets

METHOD OF MANUFACTURING A DEFLECTABLE ELECTROPHYSIOLOGICAL CATHETER

BACKGROUND OF THE INVENTION a. Field of the Invention

The present invention relates to electrophysiological (EP) catheters. More particularly, the present invention relates to a deflectable EP catheter constructed to inhibit component migration.

b. Background Art

It is known to use catheters to perform a variety of functions relating to diagnostic and therapeutic medical procedures. EP catheters find particular application in cardiac electrophysiology studies and procedures, such as various cardiac diagnostic and/or ablation procedures. In such studies/procedures, electrical signals from the heart may be conducted through electrodes disposed at the distal end of the catheter to monitoring and recording devices associated with the catheter. The electrodes may also be used for other purposes such as delivering energy to the heart as stimulus to monitor the heart's response thereto or to ablate a site of cardiac tissue that causes, for example, an arrhythmia or abnormality in the heart rhythm.

To optimize the performance of a catheter, it is important that the distal end of the catheter can deflect in one or more directions. This deflection allows for the optimal positioning of the electrodes to perform their respective function. In conventional systems, a handle portion is provided at the proximal end of the catheter. The handle portion may include an actuator that is coupled to one or more pull wires that extend to a point at or near the distal end of the catheter. The combination of the actuator and the pull wire(s) serves to selectively effectuate movement of the catheter's distal end when the actuator is selectively manipulated. It is known that the pull wires of these systems may be disposed within a lumen or lumens in the shaft portion of the catheter along with various other components, such as, for example, the wires connected to the electrodes.

These conventional arrangements, however, are not without their drawbacks. One particular drawback lies in the configuration of the lumen relative to the components disposed therein. For instance, in an arrangement wherein a plurality of electrode wires, one or more pull wires, and a flat wire (e.g., a planarity wire) are disposed within one lumen, one or more of the electrode wires may migrate into contact with a pull wire or the planarity wire and become pinched between the inner wall of the lumen and the pull wire or planarity wire. Once the wire is pinched, it cannot move as the catheter is deflected. Consequently, the wire may break, thereby disabling the functionality of the electrode that connects to the broken wire.

Accordingly, there is a need for a catheter and method of manufacturing the same that will minimize and/or eliminate one or more of the above-identified deficiencies.

BRIEF SUMMARY OF THE INVENTION

The present invention is directed to a deflectable EP catheter and a method of manufacturing the same. The catheter according to the present teachings includes a shaft having a proximal end and a distal end, and at least one lumen disposed within the shaft. The at least one lumen has a predetermined cross-sectional shape, and comprises at least one longitudinally-extending trough defined by a longitudinally-extending recess and by a longitudinally-extending open edge. The at least one lumen further comprises a longitudinally-extending channel that is defined by a longitudinally-extending cavity and by the open edge of the trough. The catheter still further includes a component disposed within the longitudinally-extending recess of the trough, and a planarity wire that is configured to close the longitudinally-extending open edge of the trough to within a pre-defined tolerance that is less than the size of the component so as to retain the component within the longitudinally-extending recess.

The method of manufacturing an EP catheter according to the present teachings includes constructing a shaft having a proximal end, a distal end, and at least one lumen disposed within the shaft. The method further includes inserting a component within the lumen, and processing at least a portion of the shaft such that the cross-sectional profile of the lumen is reduced to capture/confine the component.

A further embodiment of the method according to the present teachings includes constructing a shaft having a proximal end, a distal end, and at least one lumen disposed within the shaft. In this embodiment, the constructing step includes constructing the distal end to have a first portion and a second portion. The first portion has a first outer diameter, and at least one region of the second portion has a second outer diameter that is greater than the first outer diameter. As with the embodiment described above, this embodiment of the method further includes inserting a component in the lumen. The method still further includes processing at least the regions of the second portion of the distal end that have the enlarged second diameter such that the cross-sectional profile of the lumen is reduced to capture/confine the component disposed therein. This process causes the second outer diameter to become substantially equal to the first outer diameter.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
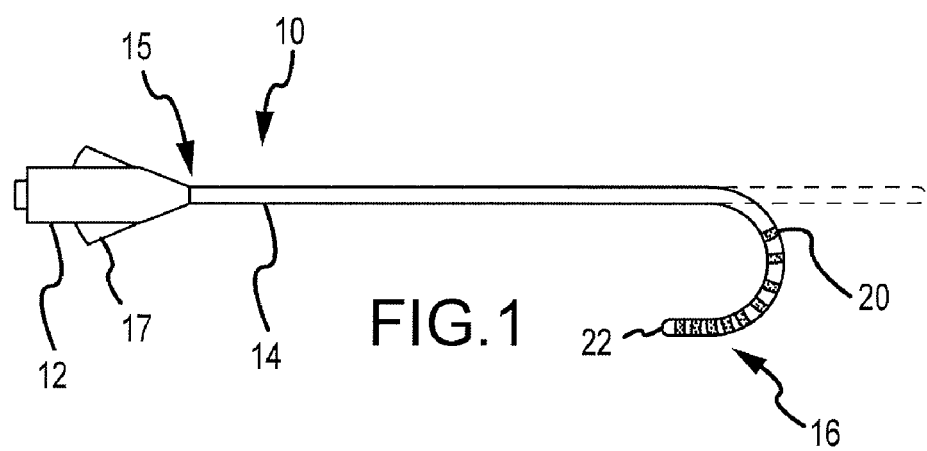
FIG. 1 is a diagrammatic view of a deflectable catheter in accordance with the present teachings.

Referring now to the drawings wherein like reference numerals are used to identify identical components in the various views, FIG. 1 illustrates one exemplary embodiment of a deflectable electrophysiological catheter 10. In its most general form, the catheter 10 includes a handle portion 12 and an elongated shaft portion 14, wherein shaft 14 extends along an axis and includes a proximal end 15 and a distal end 16. The catheter 10 may be used in a number of diagnostic and therapeutic applications, such as the recording of electrograms in the heart, the performance of a cardiac ablation procedure, and other similar applications/procedures. Accordingly, one of ordinary skill in the art will recognize and appreciate that the inventive catheter and method of manufacturing the same can be used in any number of diagnostic and therapeutic applications.

With continued reference to FIG. 1, the handle 12 is coupled to the shaft 14 at the proximal end 15. The handle 12 is operative to, among other things, effect movement (i.e., deflection) of the distal end 16. As will be described in greater detail below, the handle 12 includes an actuator 17 that can be selectively manipulated to cause distal end 16 to deflect in one or more directions (e.g., up, down, left, and right).

Figure 4:
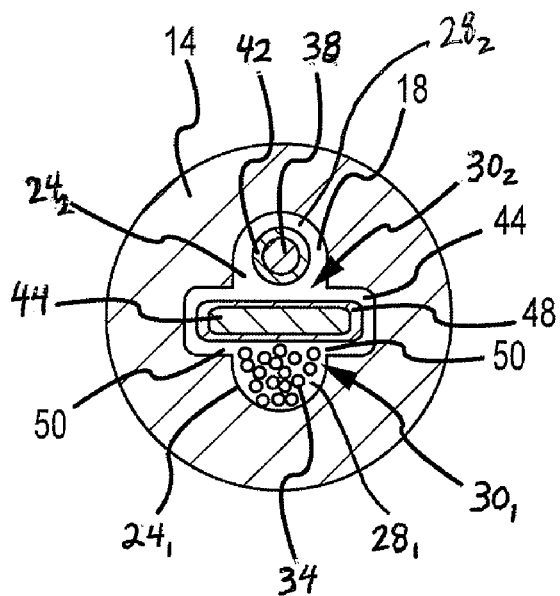
FIG. 4 is a cross-sectional view of the distal end of the catheter illustrated in FIGS. 1 and 2 taken substantially along the lines 4-4 in FIG. 2 before a process is performed on the distal end to reduce the cross-sectional profile of the lumen therein.
Figure 5:
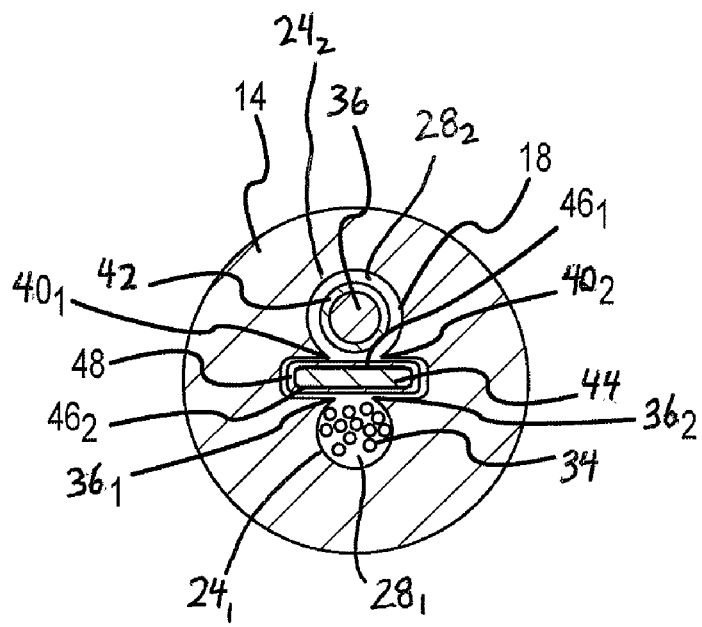
FIG. 5 is a cross-sectional view of the distal end of the catheter illustrated in FIGS. 1 and 2 taken substantially along the lines 5-5 in FIG. 2 following the performance of a process on the distal end in which the cross-sectional profile of the lumen is reduced.
Figure 6:
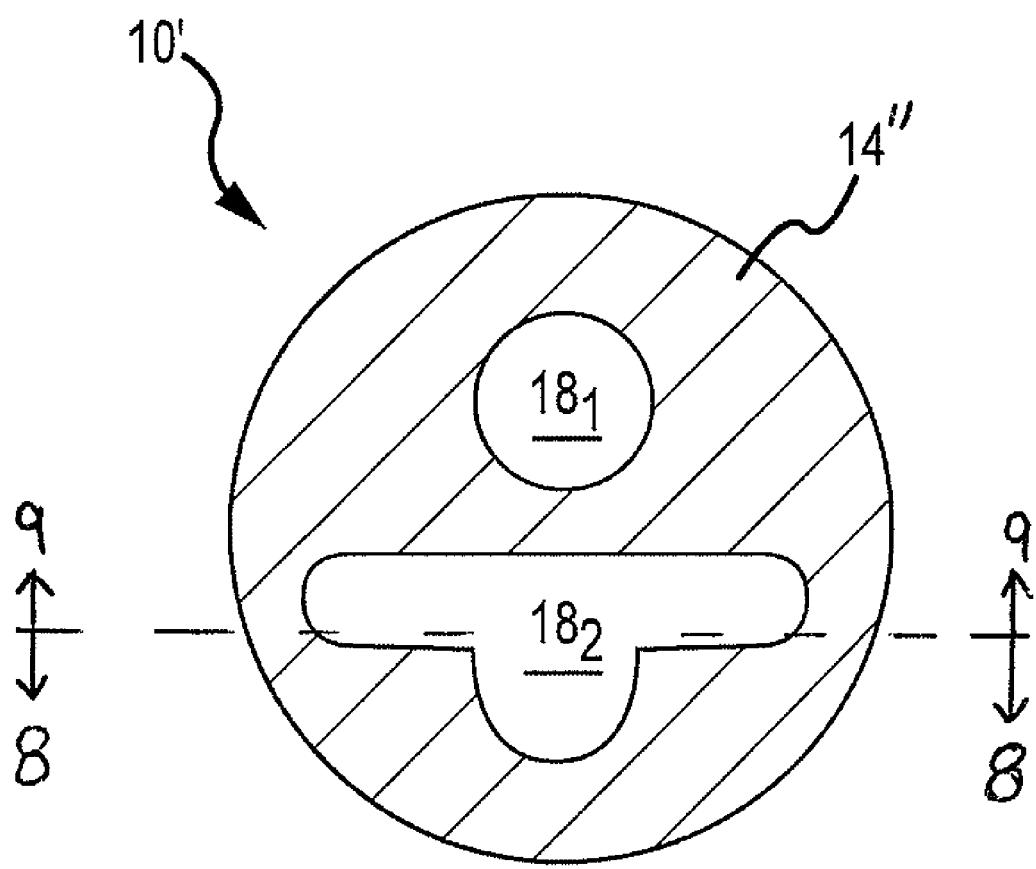
FIG. 6 is a cross-sectional view of an alternate embodiment of the catheter illustrated in FIGS. 1, 2, and 4 wherein the catheter is a multi-luminal catheter.

The catheter 10, and the shaft 14, in particular, further includes at least one lumen 18 (shown in FIGS. 4-6, for example). The lumen 18 extends longitudinally along an axial portion of the shaft 14 from the proximal end 15 to the distal end 16 and is formed to have a predetermined cross-sectional profile and size. It should be noted that depending upon the intended application of the catheter 10, the lumen 18 may extend the entire length of the shaft 14 or may extend less than the entire length. Additionally, the catheter 10 may include more than one lumen in the shaft 14 (see, for example, FIG. 6 wherein catheter 10 has two lumens, $18_1$ and $18_2$). Therefore, one of ordinary skill in the art will recognize and appreciate that the shaft 14 may have one or more lumens and/or have lumen(s) of various lengths. In an exemplary embodiment, the shaft 14 is constructed of a polymeric material, such as polyurethane, nylon, various types of plastic materials such as that offered under the trademark PEBAX®, which is a registered trademark of Arkema France, or any other suitable material. Additionally, the shaft 14 may be formed using any number of different manufacturing processes known in the art including, without limitation, extrusion processes.

Figure 2:
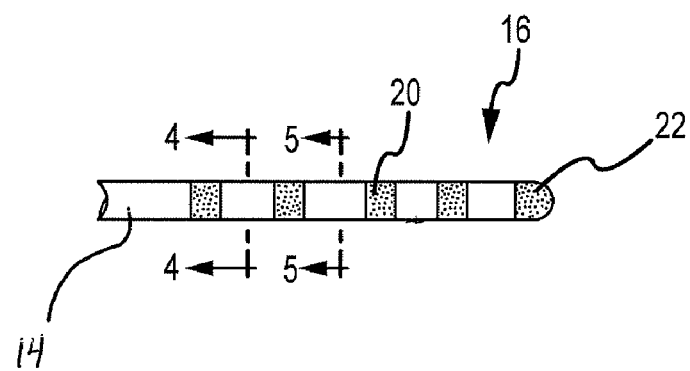
FIG. 2 is an enlarged view of the distal end of the catheter illustrated in FIG. 1.
Figure 3:
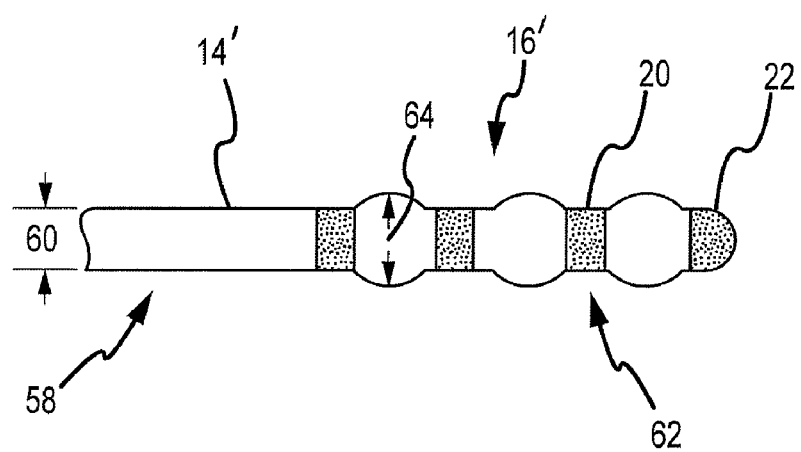
FIG. 3 is an enlarged view of an alternate embodiment of the distal end of the catheter illustrated in FIG. 1

FIGS. 2 and 3 are enlarged views of the distal end 16, 16', respectively. As shown in these figures, the catheter includes one or more electrodes (such as, for example, ring electrodes 20) mounted on or affixed to the shaft 14, 14' along the distal end 16, 16'. In these particular embodiments, the active outer surface of each electrode 20 is configured for exposure to blood and/or tissue. The electrodes 20 may be assembled with the shaft 14, 14' using any number of known processes. For instance, the electrodes 20 may be built into the shaft using a reflow process. In such a process, the electrodes 20 are placed at the appropriate/desired locations on the shaft 14, 14', and then the shaft is exposed to a heating process in which the electrodes 20 and the shaft become affixed or bonded together. As will be described below, sufficiently sized apertures are formed in the shaft proximate to each electrode 20 in order to allow for wires connected to the electrodes 20 to be threaded into the lumen 18.

In addition to, or in place of, the electrode 20, the catheter 10 may include a tip electrode 22 disposed at the extreme distal end 16, 16'. Tip electrode 22 may be configured for various functionality including, without limitation, that described above with respect to the electrodes 20. The tip electrode 22 may be affixed to distal end 16, 16' in a number of ways. For instance, the tip electrode 22 may be bonded to the inner diameter of the shaft 14, 14' (i.e., the wall of the lumen 18) using an epoxy material.

In an exemplary embodiment, protective trim (not shown) is used to cover the transitions between the electrodes 20, 22 and the shaft 14, 14'. The protective trim, which may be comprised of an epoxy material or any other suitable material, prevents sharp edges from being exposed and also prevents the ingress of blood and other fluids into the shaft 14, 14', and the lumen 18, in particular.

Figure 8:
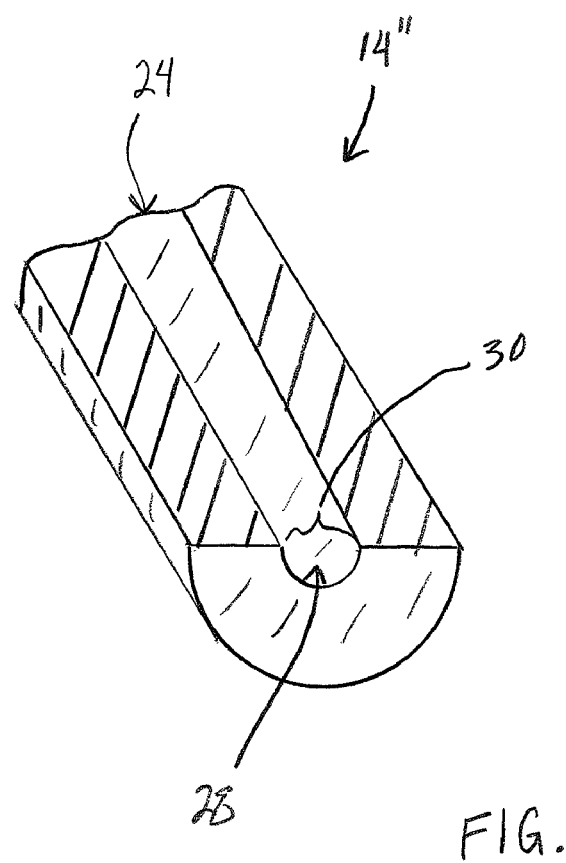
FIG. 8 is a partial cross-sectional and perspective view of the catheter illustrated in FIGS. 1, 2, 4, and 6 taken substantially along line 8-8 in FIG. 6.
Figure 9:
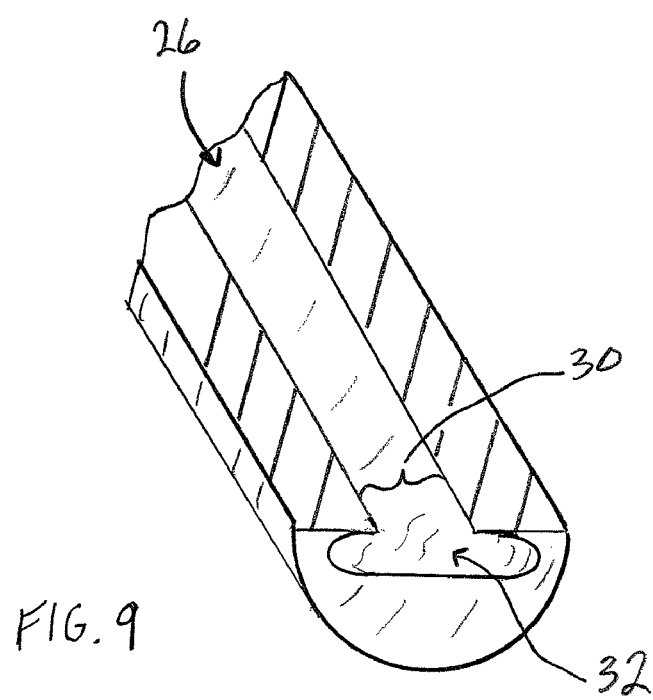
FIG. 9 is a partial cross-sectional and perspective view of the catheter illustrated in FIGS. 1, 2, 4, and 6 taken substantially along line 9-9 in FIG. 6.

FIGS. 4 and 5 are cross-sectional views of the shaft 14 of a single lumen catheter, with FIG. 4 depicting the shaft 14 prior to a process being performed on at least a portion of the shaft 14 in which the cross-sectional profile of the lumen 18 is reduced, and FIG. 5 depicting the shaft 14 following the performance of such a process. With continued reference to FIGS. 4 and 5, and also FIGS. 6, 8, and 9, in an exemplary embodiment, the lumen 18 comprises at least one longitudinally-extending trough 24 and a longitudinally-extending channel 26. The trough 24 is defined by a longitudinally-extending recess 28 and a longitudinally-extending open edge 30. The channel 26, on the other hand, is defined by a longitudinally-extending cavity 32 and the open edge 30 of the trough 24. In the exemplary embodiment illustrated in FIG. 4, the shaft 14 is constructed such that the lumen 18 has a "cross-shaped" or "t-shaped" cross-sectional profile. Thus, in this particular embodiment, lumen 18 comprises a pair of troughs 24 ($24_1$ and $24_2$), and the channel 26 is disposed between the troughs and defined, in part, by each of the open edges 30 ($30_1$, $30_2$) of the respective troughs. It should be noted that while a "cross-shaped" profile is illustrated with particularity, the present invention is not so limited. Rather, those of ordinary skill in the art will recognize and appreciate that the lumen 18 may have any number of cross-sectional profiles, such as, for example, that of lumen $18_2$ illustrated in FIG. 6, wherein lumen $18_2$ includes a single trough 24. Additionally, the lumen 18 may also be constructed such that it does not have a unitary cross-sectional shape throughout its length. Rather, different portions of the lumen 18 may have different cross-sectional profiles. In any event, the lumen 18 is configured such that various components required for performing the particular functionality of the catheter 10 (e.g., recording electrograms, ablation, ultrasound, etc.) are disposed therein (such as electrode wires, pull wires, shape wires, planarity wires, wiring for temperature sensing elements, etc.).

As briefly described above, in an embodiment wherein the catheter 10 includes one or more electrodes 20, 22 associated with the shaft 14, 14', each electrode 20, 22 includes at least one electrode or lead wire 34. The wires 34 are typically pre-coated wires such that they are insulated from each other and other components in the system. In the embodiment illustrated in FIGS. 4 and 5, the electrode wires 34 are disposed within a first trough $24_1$ of lumen 18, and more particularly, in the recess $28_1$ of the trough $24_1$. The trough $24_1$ defines a first region of the lumen 18, and the open edge $30_1$ of the trough $24_1$ serves as an opening to this region. This opening is defined by a pair of shoulders $36_1$, $36_2$ (See FIG. 5) disposed at either side thereof. In the case of an exemplary electrode 20, one end of wire 34 is connected to the electrode 20 and the other end is threaded through a corresponding aperture (not shown) in the shaft 14, 14' and into the lumen 18. The wire 34 extends through the lumen 18 and is connected to, for example, monitoring and/or recording devices associated with or connected to the catheter 10. These devices are typically located proximate to the handle 12. In the case of the tip electrode 22, the shaft 14, 14' may have an aperture therein configured to receive a wire 34 that is connected to the tip electrode 22. In either case, one end of the wire 34 is connected to the electrode 22 and the other end is threaded into the lumen 18 and connected to, for example, the monitoring or recording devices described above.

In addition to the electrode wires 34, other components may also be disposed within the lumen 18. For instance, the handle 12, and the actuator 17 in particular, may comprise at least one pull wire 38 operatively connected to it to facilitate deflection of the distal end 16. As depicted in FIGS. 4 and 5, the pull wire 38 is disposed within a second trough $24_2$ of lumen 18, and more particularly, the recess $28_2$ of the trough $24_2$. The second trough $24_2$ defines a second region of the lumen 18, different from the first region in which the electrode wires 34 are disposed. The open edge $30_2$ of the trough $24_2$ serves as an opening to this second region, and this opening is defined by a pair of shoulders $40_1$, $40_2$ disposed at either side thereof. The pull wire 38 may be surrounded by a liner 42 that serves the dual purpose of providing a lubricious surface to allow for the sliding of the pull wire 38, while also insulating the pull wire 38 from electrical wires (e.g., electrode wires 34) in the lumen 18. If provided, the liner 42 may be constructed of a polymeric material, such as polytetrafluoroethylene (PTFE), or any other suitable material. It should be noted that the catheter 10 is not limited to the single pull wire arrangement illustrated in FIGS. 4 and 5 and described above. Rather, the catheter 10 may include two or more pull wires 38 disposed within the lumen 18 to enable the distal end 16 to deflect in two or more directions.

With continued reference to FIGS. 4 and 5, the catheter 10 may further include a planarity wire 44 disposed in the channel 26 of the lumen 18 (and cavity 32 thereof, in particular). The channel 26 is located between the first and second troughs $24_1$, $24_2$, and therefore, between the first and second regions of the lumen 18 (and the openings thereof, in particular), and electrode wires 34 and the pull wire 38. The channel 26 defines a third region of the lumen 18 that is different from both the first and second regions described above (i.e., those defined by the troughs $24_1$, $24_2$). Accordingly, the lumen 18 defines an insertion tolerance between the surfaces of the planarity wire 44 and the corresponding regions of the lumen 18 to allow for the planarity wire 44 to be inserted therein. In the illustrated embodiment, the planarity wire 44 has opposing flat surfaces $46_1$, $46_2$ and serves to maintain the planarity of the shaft 14 as the shaft 14 deflects. As with the pull wire 38, the planarity wire 44 may also include a liner 48 similar to the liner 42 that serves the same purpose(s) as the liner 42. If the catheter 10 includes more than one pull wire 38, the additional pull wires would be disposed at the various sides of the planarity wire 44 so that the planarity wire 44 may maintain planarity of the shaft 14 regardless of the direction of deflection.

It should be noted that while the embodiment described above includes components that may be primarily used for diagnostic applications, components for therapeutic applications can also be disposed within the lumen 18. Accordingly, to the extent not encompassed by the description above, components used in ablation procedures, ultrasound procedures, and the like may also be disposed within the lumen 18.

Additionally, it should be further noted that the catheter 10 is not limited to a single lumen arrangement. For instance, FIG. 6 illustrates a multi-luminal catheter 10' wherein two or more lumens $18_1$, $18_2$, . . . $18_n$ are disposed within the shaft 14". In such an arrangement, the various components described above are disposed in respective lumens (the components are not shown in FIG. 6). In one particular embodiment, the lumen $18_1$ may be used as an irrigation lumen, while the lumen $18_2$, which, as briefly described above and as illustrated in FIGS. 6, 8, and 9, includes a trough 24 and a channel 26, may contain some or all of the various components described above or additional components. Alternatively, some of the components (e.g., pull wires, electrode wires, shape wires, planarity wires, etc.) may be disposed in the lumen $18_1$, while others may be disposed in the lumen $18_2$. Accordingly, those of ordinary skill in the art will recognize and appreciate that the catheter 10 may have one or more lumens 18.

For ease of description purposes only, the remainder of the description of the catheter 10 will be limited to a single-lumen arrangement. It should be noted, however, that both the foregoing and the following descriptions relating to the lumen or lumens 18 apply with equal force to both single and multi-luminal arrangements. Accordingly, the present invention is not limited solely to the single lumen arrangement described in detail above and below, but rather includes multi-luminal arrangements as well.

As described in the Background above, one disadvantage to the arrangement(s) depicted in FIGS. 4 and 6 is that there are gaps or spaces 50 between the various components disposed within the lumen 18. These gaps/spaces 50 are the result of the insertion tolerance required to allow for the insertion of the planarity wire 44 within the lumen 18, and provide a path for the electrode wires 34, for example, to migrate from a first region of the lumen 18 (i.e., the trough $24_1$, and the recess $28_1$ thereof, in particular) and into another region of the lumen 18 (i.e., the channel 26, and the cavity 32 thereof, in particular, within which the planarity wire 44 is disposed; or possibly the trough $24_2$, and the recess $28_2$ thereof, in particular, within which the pull wire 38 is disposed). When the wires 34 move into these regions, they can become pinched between the components in those regions and the inner wall of the lumen 18. Once pinched, the wires 34 may be prevented from moving freely during deflection. Consequently, the wires 34 may break, thereby rendering one or more electrodes 20, 22 disabled.

In order to combat this undesirable occurrence, at least a portion of the shaft 14, and most likely a portion of the distal end 16 having one or more electrodes 20 mounted thereon, is subjected to a process that, as will be described in greater detail below and as depicted in FIG. 5, causes the cross-sectional profile and total volume of the lumen 18 to be greatly reduced so as to capture or confine the component(s) disposed within the lumen 18, thereby having the effect of trapping and possibly encasing the components in a desired region of the lumen 18. More specifically, this process eliminates, or at least substantially reduces, the gaps/spaces 50. In an exemplary embodiment, this process comprises a heat-treating process; however, other energy-delivery processes exist (such as sonic, reflow, radio-frequency, and ultra-violet processes, as well as other known methods of polymer bonding) and may be used. Therefore, the insertion tolerance between the planarity wire 44 and a particular region of the lumen 18 (e.g., the regions defined by troughs $24_1$ and $24_2$) is reduced to a pre-defined closure tolerance that is less than the size of the component disposed within the region/trough (e.g., the size of the electrode wires 34, and/or the pull wire 38), so as to retain the component within the particular region/trough of the lumen 18. Accordingly, the migration paths of the components are eliminated, or at least substantially reduced; and, thus, the occurrence of component migration is inhibited. Additionally, because the flat surfaces $46_1$, $46_2$ of planarity wire 44 are in close proximity to the shoulders $36_1$, $36_2$ and $40_1$, $40_2$ of the openings of the first and second regions of the lumen 18 (e.g., troughs 24$_1$, 24$_2$), respectively, the movement of the planarity wire 44 away from the openings (i.e., the open edges 30$_1$, 30$_2$ of the troughs 24$_1$, 24$_2$) is restricted. Thus, the planarity wire 44 is configured to close the opening of the region/trough to within a pre-defined tolerance that is less than the size of the component so as to confine or retain the component within that region/trough, thereby further assisting with the elimination, or at least substantial reduction, of the migration paths of the component.

In an exemplary embodiment, the shaft 14 is constructed of or comprises a material that is sufficiently incompressible to prevent the components disposed within the respective regions of the lumen 18 from compressing the material so as to enlarge the closure tolerance of the lumen, thereby creating a migration path for the component. In other words, the material is such that when the catheter is deflected, the force exerted on an electrode wire and directed against the wall of lumen 18, for example, would not be sufficient to displace the shaft material to such an extent that the electrode wire would be able to slide through the reduced gaps or spaces created as a result of the process in which the cross section of the lumen is reduced.

The reduced lumen area profile prevents, or at least substantially reduces, significant lateral movement of the components, such as the electrode wires 34, within the lumen 18, and, therefore, prevents, or at least substantially reduces, the likelihood of one component migrating into a region of the lumen 18 occupied by another component. Other advantages include, for example, the reduction in size of the apertures in the shaft 14 through which electrode the wires 34 are threaded into the lumen 18, and the prevention of fluid ingress into the lumen 18, which reduces the potential for electrical noise.

Figure 7:
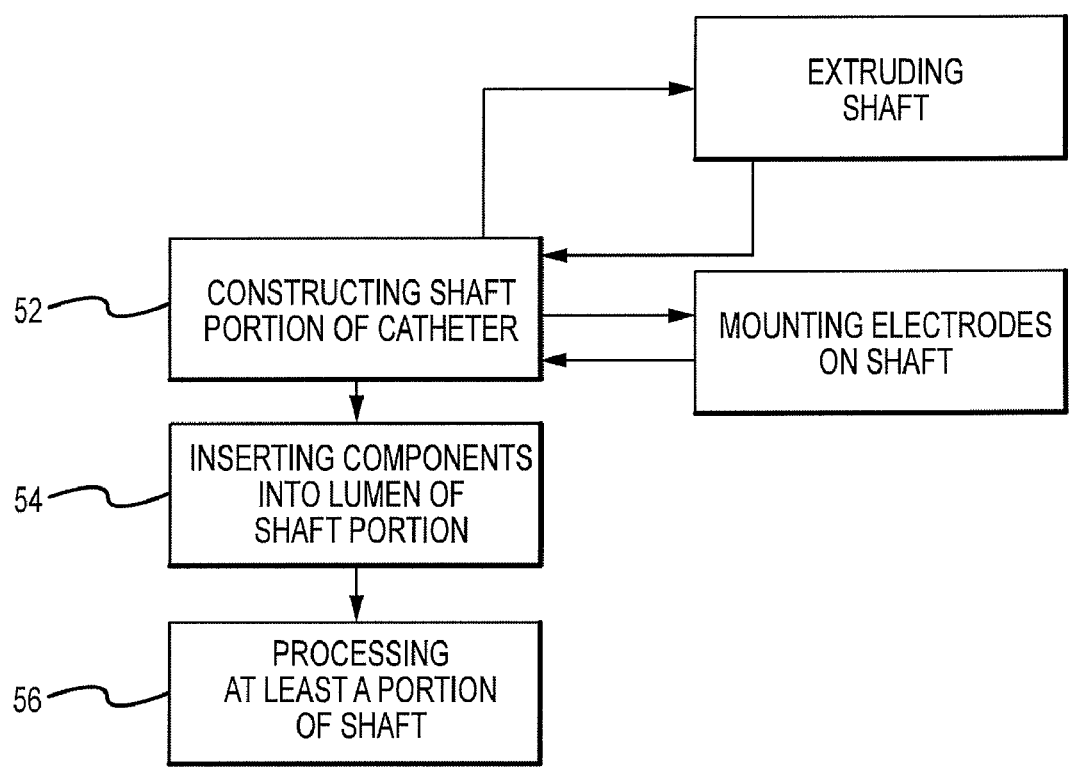
FIG. 7 is a flow diagram of a method of manufacturing the catheter illustrated in FIGS. 1-6.

With reference to FIG. 7, a method of manufacturing the catheter 10 will now be described. The exemplary method comprises a first step 52 that includes constructing the shaft portion 14. More particularly, step 52 includes constructing the shaft portion 14 to have a proximal end 15 configured for coupling with the handle 12, a distal end 16, and a lumen 18 therein. Alternatively, the shaft 14 may be constructed to have more than one lumen 18 therein so as to create a multi-luminal catheter. The lumen 18 extends along at least an axial portion of the length of the shaft 14 between the proximal end 15 and the distal end 16 and has a predetermined cross-sectional profile. The cross-sectional profile defines at least one longitudinally-extending trough 24 defined by a longitudinally-extending recess 28 and an longitudinally-extending open edge 30, and a longitudinally-extending channel 26 defined by a longitudinally-extending cavity 32 and the open edge 30 of the trough 24. In an exemplary embodiment, constructing step 52 comprises constructing the shaft 14 using an extrusion process in which a polymeric material (e.g., polyurethane, PEBAX®, nylon, etc.) is extruded to form the shaft 14. However, the present invention is not limited to such a process or material. Rather, those of ordinary skill in the art will recognize and appreciate that other processes and materials (e.g., various types of polymeric materials and/or thermoplastics) may be suitable to achieve the same result.

Regardless of the material and process used, the material and the process must be properly matched. As was briefly described above, and as will be described again below, the material must have the capability to be displaced or to shrink when subjected to a process, such as, for example, a heating process, that is performed subsequent to the constructing step. However, the constructing process must be carefully controlled so as to not generate or expose the shaft 14 to an excessive amount of heat that would cause the shaft material to be reflowed or shrunk during the construction process itself. Accordingly, the material must be able to withstand exposure to any heat generated in the construction process such that the material is reflowed or shrunk in a subsequent process rather than in the shaft construction process.

In an exemplary embodiment, step 52 further includes constructing the shaft 14 with at least one electrode 20 and/or tip electrode 22 thereon as was described in greater detail above. Alternatively, the electrodes 20, 22 are affixed to and/or mounted on the shaft 14 in a subsequent step.

A second step 54 includes inserting at least one component into one or more lumens 18 of the shaft 14. In an exemplary embodiment, the components inserted and disposed within the lumen 18 include, as described above, at least one electrode wire 34, at least one pull wire 38, and/or a planarity wire 44. However, in other embodiments, the components within the lumen 18 may take the form of any number of different or additional articles/devices typically present in catheters used for diagnostic or therapeutic purposes (e.g., shape wires, wires corresponding to temperature sensing elements, etc.). In the embodiment wherein the components include the electrode wire 34, the pull wire 38, and the planarity wire 44, each component is disposed within a respective region of lumen 18 (i.e., a respective trough 24 for each of the electrode wire 34 and the pull wire 38, and the channel 26 for planarity wire 44), with the planarity wire region being located between the electrode wire region and the pull wire region. Accordingly, the constructing step 52 includes the substep of providing a lumen so as to establish an insertion tolerance between the surfaces of a planarity wire and corresponding regions of the lumen to allow for the insertion of the planarity wire.

A third and final step 56 includes processing at least a portion of the shaft 14 such that, as described above, the cross-sectional profile of the lumen 18 is reduced so as to eliminate or at least substantially reduce the gaps between the respective regions of the lumen 18, and, therefore, reduce the potential migration paths of the electrode wires 34, thereby capturing/confining the component(s) disposed within the lumen 18. Accordingly, the processing step 56 is operative to reduce the aforementioned insertion tolerance to a pre-defined closure tolerance wherein the closure tolerance is less than the size of the component(s) disposed within the lumen 18. In an exemplary embodiment, the processing step 56 comprises a heating process and it is applied to the distal end 16. The processing step 56 may further comprise a heating process that includes reflowing a portion of the shaft 14.

In an alternate exemplary embodiment depicted in, for example, FIG. 3, the constructing step 52 includes constructing a shaft 14' to have a first portion 58 having a first outer diameter 60 and a second portion 62 wherein at least certain regions thereof have a second outer diameter 64 that is larger than first diameter 60. Accordingly, the shaft 14' is constructed such that one or more regions (e.g., the regions between electrodes 20, 22) of the second portion 62 contain more shaft material than first portion 58. In such an embodiment, the processing step 56 comprises processing the second portion 62 such that as the cross-sectional profile of the lumen 18 is reduced, the material closest to the components and that comprises the inner wall of the lumen is displaced to create the reduced cross-sectional profile. As this material is displaced, the void created by the displaced material is filled with the extra material that forms enlarged regions of the second portion 62 that have the enlarged second diameter 64. In such an embodiment, once the processing step 56 is complete, the outer diameter 64 of second portion 62 is substantially the same as the outer diameter 60 of first portion 58 (See FIG. 2). This ensures a smooth outer surface of shaft 14.

As briefly described above, the processing step 56 may include any number of energy-delivery processes, such as, for example, heat-treating, reflow, sonic, radio-frequency, ultraviolet, or other any other suitable processes, or other known methods of polymer bonding, that are suitable for causing the cross-sectional profile of the lumen 18 to be reduced, thereby capturing/confining the components therein.

In an alternate exemplary embodiment, an intervening step is performed prior to the processing step 56 that includes placing a shrink tube over the portion of shaft 14 that is to be exposed to an energy delivery process, for example, rather than having the shaft 14' constructed to include the enlarged diametered regions. As energy is delivered and applied during the processing step 56, the shrink tube constricts and melts into the surface of the shaft 14. In this manner, the shrink tube may serve to fill the voids in shaft 14 that were left by the reduction in the cross-sectional profile of the lumen 18.

An additional step, which may be performed after the shaft 14 is processed, or any time before, includes coupling the shaft 14 with the handle 12. Those of ordinary skill in the art will recognize and appreciate that any number of coupling methods may be used to carry out this step.

Although only certain embodiments of this invention have been described above with a certain degree of particularity, those skilled in the art could make numerous alterations to the disclosed embodiments without departing from the scope of this invention. For example, other process may be used to construct and assemble catheter 10. Further, various types of energy-delivery processes may be employed to carry out the processing function described above. Still further, different types of catheters may be manufactured or result from the inventive process described in detail above. For instance, catheters used for diagnostic purposes and catheters used for therapeutic purposes may both be manufactured using the inventive process. Additionally, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. A method of manufacturing a deflectable electrophysiological catheter, the method comprising the steps of
    constructing a shaft having a proximal end, a distal end, and a lumen having a cross-sectional profile;
    inserting a component within said lumen; and
    processing at least a portion of said shaft such that the cross-sectional profile of said lumen is reduced to confine said component, wherein
    said constructing step further comprises providing said lumen so as to establish an insertion tolerance between surfaces of a planarity wire and corresponding regions of said lumen to allow for the insertion of said planarity wire; and
    said processing step further comprises reducing said insertion tolerance to a closure tolerance, wherein said closure tolerance is less than a size of said component disposed within said lumen.

2. The method of claim 1, wherein said processing step further comprises employing an energy delivery process.

3. The method of claim 2, wherein said method further includes the step of placing a shrink tube over said portion of said shaft prior to said processing step.

4. The method of claim 1, wherein said constructing step comprises constructing said shaft to have a plurality of lumens.

5. The method of claim 1, wherein said constructing step includes constructing said shaft such that said lumen has a cross-shaped cross-sectional profile.

6. The method of claim 1, wherein said inserting step further comprises inserting an electrode wire in said lumen.

7. A method of manufacturing a deflectable electrophysiological catheter, the method comprising the steps of
    constructing a shaft having a proximal end, a distal end, and a lumen having a cross-sectional profile;
    inserting a component within said lumen; and
    processing at least a portion of said shaft such that the cross-sectional profile of said lumen is reduced to confine said component, wherein
    said constructing step further comprises constructing a shaft having a first portion with a first outer diameter and a second portion, wherein a region of said second portion has a larger outer diameter than said first outside diameter; and
    said processing step further comprises processing said second portion such that when said cross-sectional profile is reduced, the material of said second portion is displaced and said larger outer diameter of said region of said second portion becomes substantially equal to the first outer diameter of said first portion.

8. A method of manufacturing a deflectable electrophysiological catheter, the method comprising the steps of
    constructing a shaft having a proximal end, a distal end, and a lumen having a cross-sectional profile;
    inserting a component within said lumen; and
    processing at least a portion of said shaft such that the cross-sectional profile of said lumen is reduced to confine said component, wherein
    said inserting step further comprises inserting at least one electrode wire in a first longitudinally-extending trough of said lumen; and wherein said method further comprises
        inserting a pull wire in a second longitudinally extending-trough of said lumen,
        inserting a planarity wire in a longitudinally-extending channel of said lumen that is located between said first and second longitudinally-extending troughs, and
        affixing an electrode on said distal end of said shaft.

9. A method of manufacturing a deflectable electrophysiological catheter, the method comprising the following steps:
    constructing a shaft having
        a proximal end,
        a distal end comprising
            a first portion having a first outer diameter, and
            a second portion having a region with a second outer diameter that is greater than said first outer diameter; and
        a lumen comprising a cross-sectional profile and extending along said distal end;
    inserting a component within said lumen; and processing said second portion of said distal end such that said cross-sectional profile of said lumen is reduced to confine said component, and said second outer diameter of said region of said second portion becomes substantially equal to said first outer diameter of said first portion.

10. The method of claim 9, wherein
said constructing step further comprises providing said lumen so as to establish an insertion tolerance between surfaces of a planarity wire and corresponding regions of said lumen to allow for the insertion of said planarity wire; and
said processing step is operative to reduce said insertion tolerance to a closure tolerance, wherein said closure tolerance is less than a size of said component disposed within said lumen.

11. The method of claim 9, wherein said processing step comprises employing an energy delivery process.

12. The method of claim 11 further comprising the step of placing a shrink tube over said second portion of said shaft prior to said processing step.

13. The method of claim 9, wherein said constructing step further comprises constructing said shaft to have a plurality of lumens.

14. The method of claim 9, wherein said constructing step further comprises constructing said shaft such that said lumen has a cross-shaped cross-sectional profile.

15. The method of claim 9, wherein said inserting step includes inserting an electrode wire within said lumen.

16. The method of claim 9, where said constructing step further comprising affixing an electrode on said distal end of said shaft, and wherein said inserting step further comprises inserting an electrode wire in a first longitudinally-extending trough of said lumen; said method further comprising
inserting a pull wire in a second longitudinally-extending trough of said lumen,
inserting a planarity wire in a longitudinally-extending channel of said lumen that is located between said first and second longitudinally-extending troughs; and
affixing an electrode on said distal end of said shaft.

* * * * *